United States Patent [19]

Schultz et al.

[11] Patent Number: 5,429,936
[45] Date of Patent: Jul. 4, 1995

[54] ANTIBODY-MEDIATED JUXTAPOSITION OF REACTIVE MOIETIES

[75] Inventors: Peter G. Schultz, Oakland; Paul A. Bartlett, Kensington, both of Calif.

[73] Assignee: The Regents of the University of California, Oakland, Calif.

[21] Appl. No.: 341,783

[22] Filed: Apr. 21, 1989

[51] Int. Cl.6 .............................................. C12N 9/00
[52] U.S. Cl. .................................. 435/188.5; 435/233; 530/388.9
[58] Field of Search ................... 435/233, 135, 188.5; 530/387, 388, 388.9

[56] References Cited

U.S. PATENT DOCUMENTS 4,888,281 12/1989 Schochetman et al. ............... 435/72
4,900,674 2/1990 Benkovic et al. .................... 435/232
5,030,717 7/1991 Tramontano et al. ............... 530/387

OTHER PUBLICATIONS

Pollack et al., "Selective Chemical Catalysis by an Antibody", Science, 19 Dec. 1986, vol. 234, pp. 1570–1573.
Pollack et al., "Antibody Catalysis by Transition State Stabilization", Cold Spring Harbor Symposia, vol. LII, 1987, pp. 97–104.
Napper et al., "A Stereospecific Cyclization Catalyzed by an Antibody", Science, vol. 237, pp. 1041–1043 (1987).
Tramontano et al., "Catalytic Antibodies", Science, vol. 234, pp. 1566–1570 (1986).
Tramontano et al., "Antibody Catalysis Approaching the Activity of Enzymes", J. Am. Chem Soc., vol. 110, 1988, pp. 2282–2286.
Jackson et al., "An Antibody–Catalyzed Claisen Rearrangement", J. Am. Chem. Soc., 1988, 110, 4841.
Janda et al., "Antibody Catalysis of Bimolecular Amide Formation", J. Am. Chem. Soc., 1988, 110, 4835–4837.
Hilvert et al., "Catalysis of Concerted Reactions by Antibodies: The Claisen Rearrangement", Proc. Natl. Acad. Sci, vol. 85, pp. 4953–4955.
Janda et al., "Induction of an Antibody that Catalyzes the Hydrolysis of an Amide Bond", Science, vol. 241, pp. 1188–1191 (1988).
Napper et al., "A Stereospecific Cyclization Catalyzed by an Antibody", Science, vol. 237, 28 Aug. 1987, pp. 1041–1043.
Benkovic et al., "Catalysis of a Stereospecific Bimolecular Amide Synthesis by an Antibody", Proc. Natl. Acad. Sci., vol. 85, Aug. 1988, pp. 5355–5358.
Nisonoff et al., "The Antibody Molecule", Academic Press, N.Y. (1975) pp. 23–27.
Schultz, "The Interplay Between Chemistry and Biology in the Design of Enzymatic Catalysts", Science, vol. 240, 22 Apr. 1988, pp. 426–433.
Bartlett, P. A., et al. (1988) J. Org. Chem 53, 3195–3210.
Bartlett, P. A., et al. (1985) J. Am. Chem. Soc. 107, 7792–7793.

Primary Examiner—Charles L. Patterson, Jr.
Attorney, Agent, or Firm—Townsend and Townsend Khourie and Crew

[57] ABSTRACT

A variety of chemical reactions are rate enhanced by the use of antibodies whose antibody binding sites are complementary to the reactant orientations or transition states which lead to the desired product. The reactions include pericyclic reactions such as Claisen and Cope rearrangements and Diels Alder reactions, peptide bond hydrolysis reactions, peptide fragment ligations, lactonizations and cyclic peptide syntheses, glycosylations, aldol additions, nucleoside syntheses and transesterification reactions. Haptens which are stable analogues of unstable transition states, or which are analogues of desired products, in some cases with leaving groups still attached for purposes of avoidance of product inhibition, are used to generate the antibodies.

11 Claims, 12 Drawing Sheets

TRANSITION STATE

HAPTEN

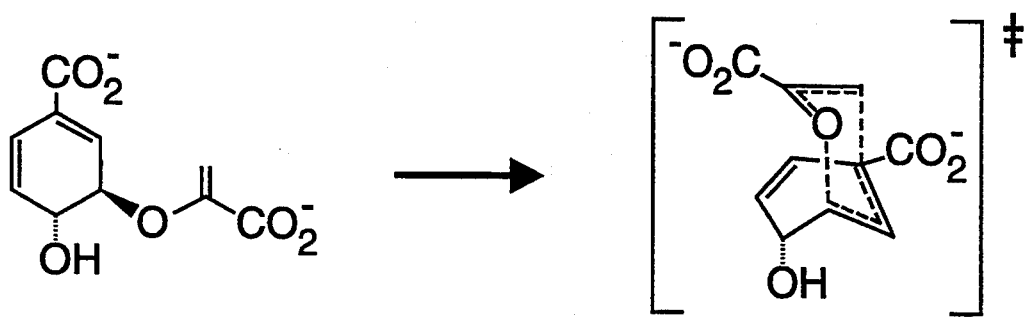
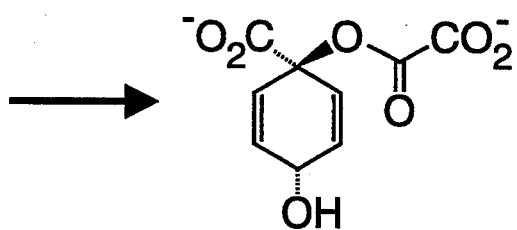
TRANSITION STATE
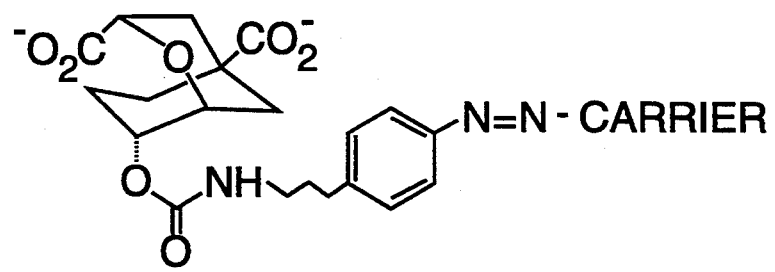
HAPTEN
Fig. 1

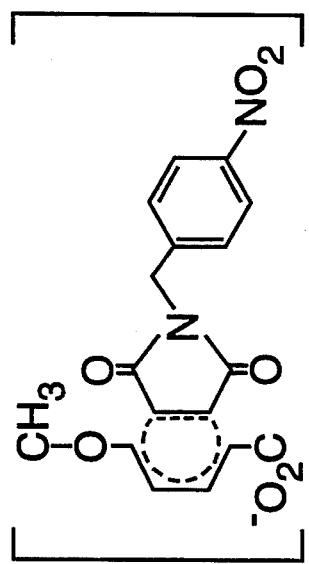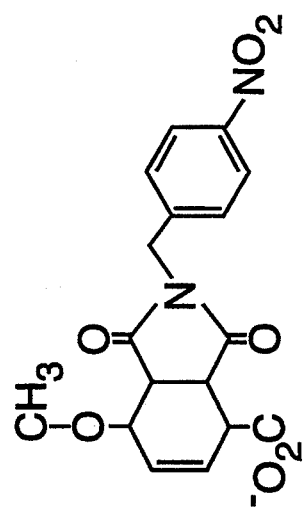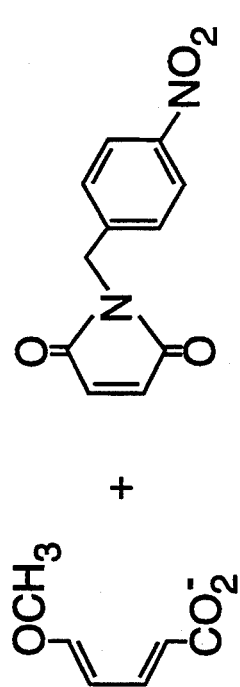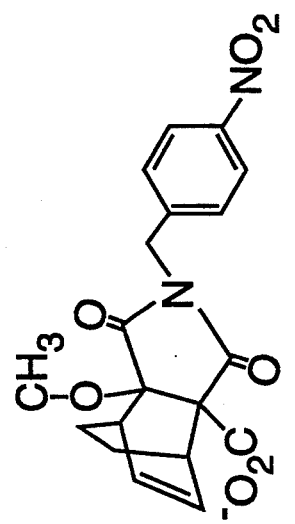
*Fig. 2*
TRANSITION STATE
HAPTEN

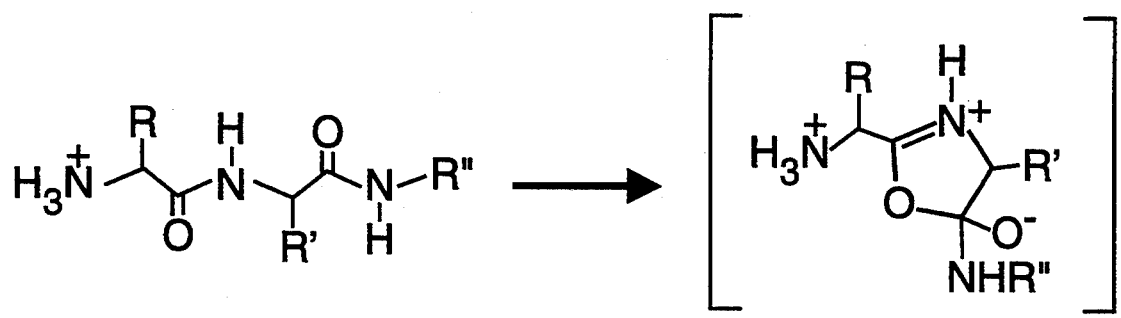
TRANSITION STATE
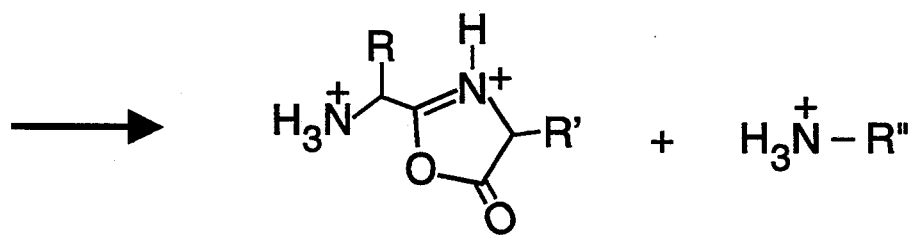
Fig. 3
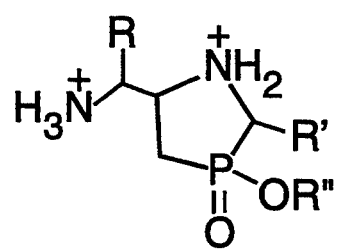
HAPTEN
Fig. 4

TRANSITION STATE

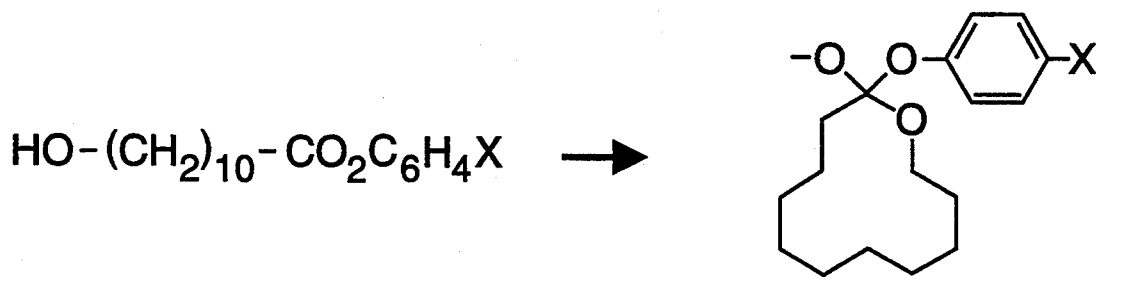
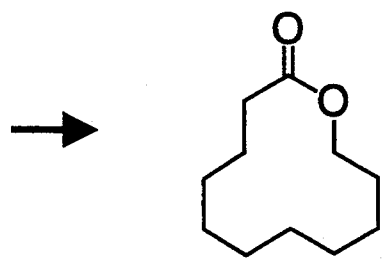
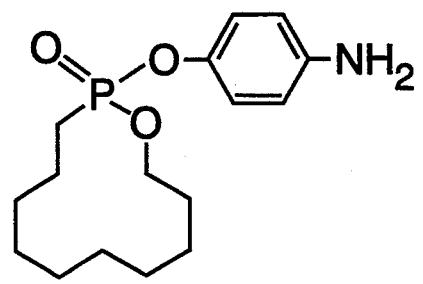
HAPTEN
Fig. 7

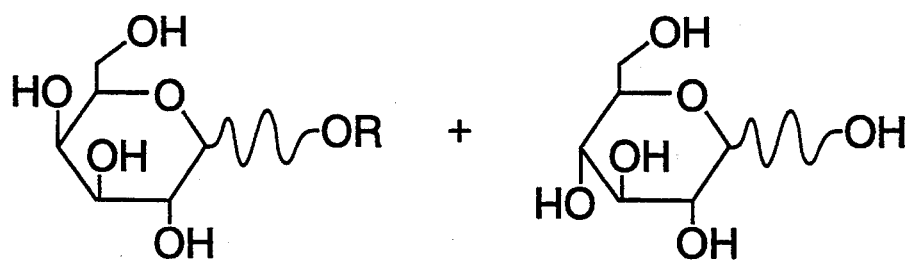
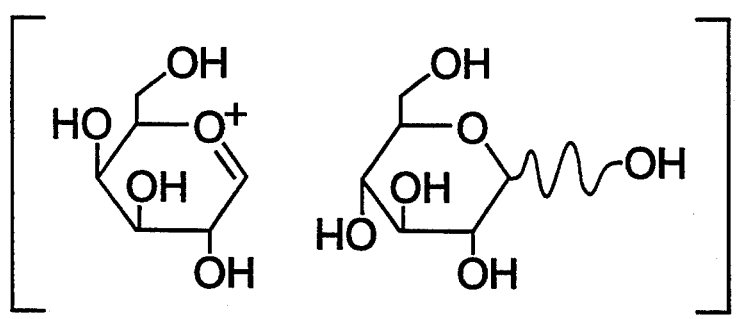
REACTIVE INTERMEDIATE SPECIES
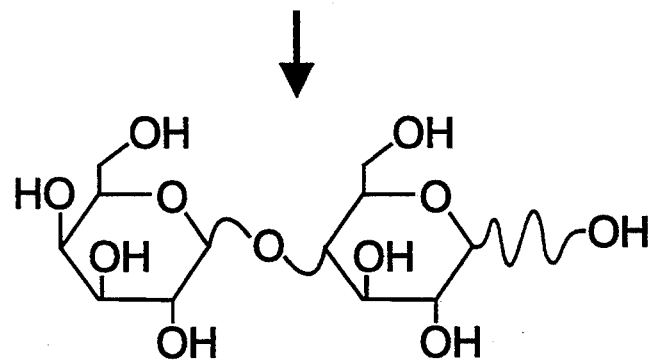
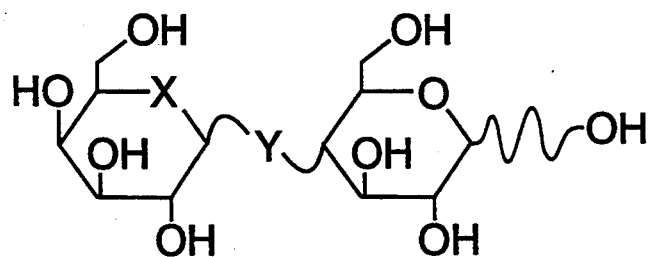
HAPTEN
Fig. 8

REACTIVE INTERMEDIATE SPECIES

Fig. 9    HAPTEN

HAPTEN

ANTIBODY-MEDIATED JUXTAPOSITION OF REACTIVE MOIETIES

This invention was made with Government support under Grant Contract No. AI-24695, awarded by the Department of Health and Human Services, and under Grant Contract No. N 0014-87-K-0256, awarded by the Office of Naval Research. The Government has certain rights in this invention.

Commonly owned copending application Ser. No. 07/273,455 and Ser. No. 07/273,786, both filed Nov. 18, 1988, contain subject matter of possible relevance to the present invention.

BACKGROUND OF THE INVENTION

1. Field of the Invention

This invention relates to the use of antibodies as rate-enhancing agents in the performance of chemical reactions. In particular, this invention relates to certain particular types of chemical reactions, and to the use of the antibody binding specificity itself in placing the reactive moieties in the specific orientations and/or transition states needed to cause these reactions to occur and lead to the desired product.

2. Description of the Relevant Art

The preparation of catalytic antibodies against certain haptens that are transition state analogues is described in: Pollack, et al. (1986) *Science* 234: 1570–1573; Pollack, et al. (1987) *Cold Spring Harbor Symp. Quant. Biol.* 52: 97–104; Jacobs, et al. (1987) *J. Am. Chem. Soc.* 109: 2174–2176; Tramontano, et al. (1986) *Science* 234: 1566–1570; Tramontano, et al. (1988) *J. Am. Chem. Soc.* 110: 2282–2286; and Janda, et al. (1988) *Science* 241: 1188–1191. The use of antibodies to overcome entropic barriers in a lactonization reaction is discussed in Napper, et al. (1987) *Science* 237: 1041–1043; and in further systems involving the orientation of reaction partners in: Jackson, et al. (1988) *J. Am. Chem. Soc.* 110: 4841–4842; Janda, et al. (1988) *J. Am. Chem. Soc.* 110: 4835–4837; Hilvert, et al. (1988) *Proc. Natl. Acad. Sci. USA* 85: 4953–4955; and Berkovic, et al. (1988) *Proc. Natl. Acad. Sci. USA* 85: 5355–5358. Antibodies generated against positively charged haptens containing complementary aspartate and glutamate residues are discussed in Nisonoff, et al. (1975) *The Antibody Molecule*, Academic Press, pp. 23–27.

The experimental data in Example 1 was published in Schultz (22 Apr. 1988) *Science* 240: 426–433.

SUMMARY OF THE INVENTION

It has now been discovered that certain types of chemical reactions not heretofore conducted in the presence of antibodies are susceptible to rate enhancements by antibody binding. The antibodies achieve this by restricting the rotational and translational motions of the reacting groups in both intermolecular and intramolecular reactions, thereby creating a large effective concentration of the reacting groups at the antibody binding sites. The antibodies thus lower the entropic barriers which govern the reaction rate, or, stated another way, provide an entropic driving force for the reaction.

The effect of the antibody will generally be to reduce rotational and/or translational degrees of freedom of the reacting groups with respect to each other. Depending on the particular type of reaction involved, this effect may be one which favors a specific transition state over alternative transition states, stabilizes an otherwise highly or relatively unstable transition state, favors a specific orientation of reactant partners over alternative orientations, or restricts conformational degrees of freedom. The resulting rate enhancements extend to both intramolecular and intermolecular reactions, including rearrangements, cyclizations, condensations, cleavages, ligations, additions, eliminations, and exchanges. Likewise, the rate enhancements extend to substrates which are both unimolecular and multimolecular, ranging in size from relatively small molecules of ten atoms or less to macromolecules such as proteins, hormones, polysaccharides and polynucelotides.

Methods of eliciting the antibodies involve the use of haptens designed to approximate the steric and electronic conformations of the reactive moieties needed for the reactions to proceed. In certain cases, the hapten will thus be a stable analogue of the transition state sought to be stabilized, the analogue made stable by the replacement of an unstable center with a stable group of similar size, shape, orientation and electronic configuration. In further cases, the hapten will be an analogue of a specific intermediate structure among two or more intermediate structures of which those other than the chosen structure lead to products other than the desired product. The hapten in such cases will be one which is readily synthesized and isolated in high purity. In still further cases, the hapten will be a hybrid or conjugated structure containing moieties analogous to two or more reaction partners, the moieties joined either directly or through linking groups which fix them in relative positions, both in terms of orientation and distance, which closely approximate the relative positions of the reaction partners required for the desired reaction to proceed. Still further types of haptens and the microenvironments which they create will become apparent from the description which follows.

The present invention further entails in certain cases the discovery of stable haptens bearing the characteristics described above, and their use in eliciting the appropriate antibodies. In some of the reactions disclosed herein, the haptens are specifically designed to elicit antibodies which, although enhancing the progress of the reaction and the formation of the desired product, avoid product inhibition of the antibody binding capacity. This effect is also achieved in some cases by appropriate selection of the reactive species among alternative systems all of which are capable of forming the desired product.

The use of the haptens in generating the antibodies follows conventional procedures involving host immunization. The haptens are generally coupled to carrier molecules which render them immunogenic, the coupling achieved through conventional linking groups or spacer arms. The use of monoclonal antibodies offers advantages in both quantity and specificity.

BRIEF DESCRIPTION OF THE DRAWINGS

FIG. 1 illustrates a Claisen rearrangement susceptible to acceleration by the invention, including the transition state and a hapten suitable for generating the appropriate antibody.

FIG. 2 illustrates a Diels Alder reaction susceptible to acceleration by the invention, including the transition state and a hapten suitable for generating the appropriate antibody.

FIG. 3 illustrates one type of peptide cleavage reaction susceptible to acceleration by the present invention, including the transition state.

FIG. 4 illustrates a hapten suitable for generating an antibody capable of accelerating the reaction shown in FIG. 3.

FIG. 7 illustrates a lactonization reaction susceptible to acceleration by the invention, including the transition state and a hapten suitable for generating the appropriate antibody.

FIG. 8 illustrates one type of glycosylation reaction susceptible to acceleration by the invention, including the reactive intermediate species and a hapten suitable for generating the appropriate antibody.

DETAILED DESCRIPTION OF THE INVENTION AND PREFERRED EMBODIMENTS

1. Pericyclic Reactions

Figure 5:
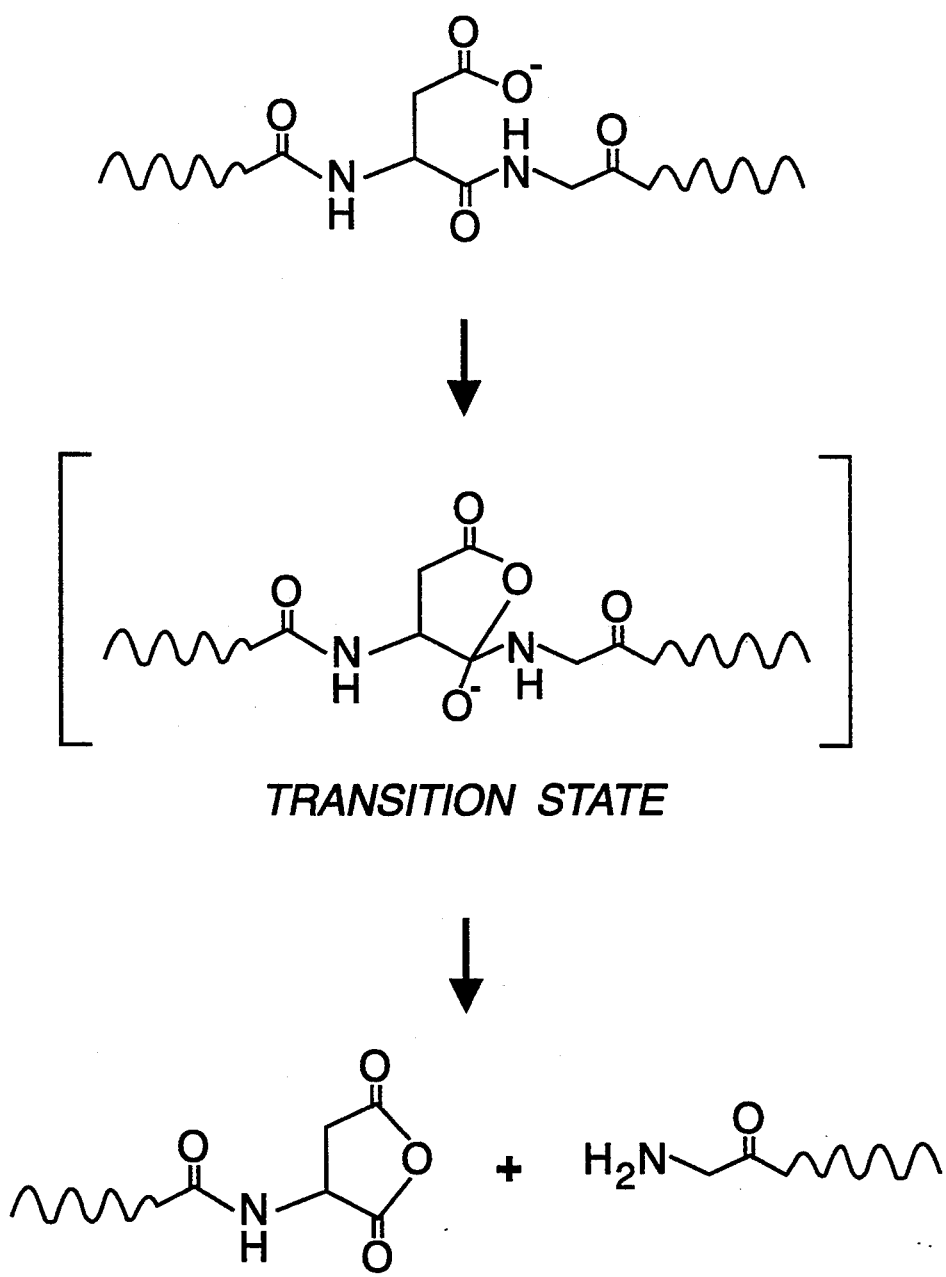
FIG. 5 illustrates a second type of peptide cleavage reaction susceptible to acceleration by the present invention, including the transition state.

The present invention is applicable to pericyclic reactions, i.e., reactions involving the redistribution of electrons between doubly and singly bonded and non-bonded atoms by passing through a cyclic transition state. The invention resides in the use of antibodies to conformationally restrict the reactants into a chair-like structure, thereby lowering the entropic barriers to the conversions from reactant to product.

Typical pericyclic reactions are those in which the cyclic portion of the transition state includes bonds which are neither single bonds nor double bonds, but rather have partial single or double bond character. The ring will thus include bonds which are not fully formed or broken, such as those which are less than a single bond, those which are more than a single bond but less than a double bond. Certain rings will contain both types of bonds. Notable examples of electron redistributions occurring through such cyclic transition states are those in which a pair of double bonds, present either as double bonds in a single molecular species or as one double bond each in two species of a reactant pair, are converted to single bonds while the excess electrons convert one or more preexisting single bonds to double bonds, or form a single bond between two previously unjoined atoms.

Depending on the reaction, the cyclic portion may consist entirely of carbon atoms, or may contain hetero atoms such as oxygen or nitrogen. The cyclic portion may range in size, most notably from five-membered rings upward. Six-membered rings are particularly common, and therefore preferred. The conformation of the ring may also vary, depending on the nature of the bonds as well as the number of atoms in the ring, with a view toward the configuration of the desired product. In six-membered rings, for example, the desired ring may be planar or may have a chair-like or boat-like configuration.

The pericyclic reactions susceptible to rate enhancement by the present invention extend to both intramolecular rearrangements and intermolecular combinations. The utility of, and advantage offered by, the present invention will increase as the entropy barrier of the reaction in its uncatalyzed form increases. Stated in terms of the free entropy of activation of the reaction, and noting that this free entropy is a negative value, this is equivalent to stating that the advantage increases as the free energy of activation decreases, or as its absolute value increases. Accordingly, for intramolecular rearrangements, the present invention is of particular utility where the free entropy of activation for the uncatalyzed reaction is less than about $-5$ eu, and preferably less than about $-10$ eu. For intermolecular reactions, those where the free entropy of activation is less than about $-10$ eu are preferred, particularly those where the free entropy of activation is less than about $-25$ eu.

One example of an intramolecular pericyclic reaction is a Claisen rearrangement. This includes both the rearrangement of alkenyl ethers of enols to $\gamma,\delta$-unsaturated ketones, and the rearrangement of alkenyl ethers of phenols to o-alkenylphenols. A generic representation of the former is as follows:

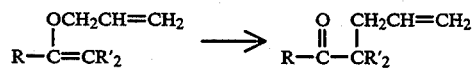

A generic representation of the latter is as follows:

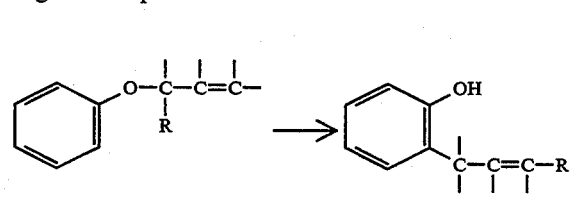

One example of the first type of reaction described above is the rearrangement of a cycloalkenyl ether of an enol to a $\gamma,\delta$-unsaturated ketone, and in particular the rearrangement of a 2,4-cyclohexadienyl ether of an enol to a $\beta$-2,5-cyclohexadienyl ketone. An example of the latter is the rearrangement of chorismate, trans-3-[(1-carboxyethenyl)oxy]-4-hydroxy-1,5-cyclohexadiene-1-carboxylic acid, to prephenate, 1-carboxy-4-hydroxy-$\alpha$-oxo-2,5-cyclohexadiene-1-propanoic acid. The transition state for the 2,4-cyclohexadienyl ether rearrangement is a bicyclic species, the added ring being a six-membered O-containing heterocycle, four sides of which are bonds between single and double and the remaining two sides of which are bonds which are less than single, the ring having a chair-like conformation. An appropriate hapten for the generation of an antibody which will restrict the chorismic ground state conformation into the chair-like transition state is one which has an identical bicyclic structure, with the O-containing heterocycle being formed entirely of single bonds.

Other haptens may contain cyclic groups having double bonds, or a combination of single and double bonds. The hapten will be modified by a suitable spacer arm to permit conjugation to a carrier protein. These and other haptens are prepared by conventional techniques.

A structural representation of the chorismate rearrangement, including its transition state and an appropriate hapten, is shown in FIG. 1.

A further example of an intramolecular pericyclic reaction is a Cope rearrangement, defined herein as including oxy-Cope rearrangements. This generally includes the rearrangement of a 1,5-diene, resulting in reorientation of the substituents with respect to the double bonds. In the case of oxy-Cope rearrangements, a typical system is the rearrangement of a hydroxy-1-alken-5-yne to an oxo-2,4-diene. The transition state in each case is a cyclohexyl structure with partially formed single and partially formed and/or broken double bonds (and, in the case of oxy-Cope, partially broken triple bonds), generally in a chair-like conformation. An appropriate hapten may be an analogue of the transition state in which the cyclohexyl ring is composed entirely of single bonds in the chair conformation. This and other haptens for antibodies to Cope rearrangements are prepared by conventional techniques.

An example of an intermolecular pericyclic reaction is a Diels Alder reaction. The microenvironment in the antibody binding site for this type of reaction in accordance with the present invention is one which holds the diene and dienophile in a fixed reactive conformation favoring the formation of the six-membered ring product. To achieve this microenvironment, the antibody is elicited by a hapten which mimics both the cisoid conformation of the diene and the overlapping $\pi$ systems of the diene and dienophile. One type of hapten which does this is one which includes a bicyclooctene ring system which resembles the $6\pi$ electron transition state of the reaction. Inclusion of the ethano bridge forces the hapten to resemble the "boat" conformation of the diene-dienophile reactive complex but not the cyclohexene product, thereby avoiding product inhibition. An example of such a hapten and the reaction which would be enhanced by an antibody raised against the hapten is shown in FIG. 2. This and other haptens of similar effect are prepared by conventional techniques.

In Diels Alder reactions involving an asymmetrical diene and dienophile which could otherwise combine in different ways, the present invention is also useful in exerting stereochemical control over the reactants, i.e., endo vs. exo additions. The hapten may thus be selected with substituents corresponding to those of the desired isomer, i.e., with the substituents in preselected locations with respect to each other and the bond corresponding to the double bond, thereby producing an antibody favoring only that isomer.

As in other types of reactions, the invention is of greatest utility for Diels Alder reactions having a high entropic barrier. Preferred such reactions in the context of this invention are those for which the free entropy of activation for the uncatalyzed reaction is less than about −25 eu.

2. Peptide Cleavage Reactions

Peptide bond hydrolysis reactions, particularly those involving a transition state containing a heterocyclic ring, are rate enhanced by the present invention in a variety of ways. One hydrolysis method to which this may be applied is that involving the formation of an oxazolone ring by the carbonyl oxygen of one amide group linking with the carbonyl carbon of an adjacent amide group. The transition state leading to the oxazolone is a labile intermediate containing a five-membered heterocyclic ring containing a nitrogen atom, an oxygen atom, and three carbon atoms, one of the carbon atoms being a chiral tetrahedral carbon atom bonded to the ring oxygen, one of the ring carbons, and a nitrogen and oxygen atom outside the ring. A generic structural representation of the oxazolone formation including the labile intermediate is shown in FIG. 3, where the R groups are amino acid side chains.

In accordance with the invention, an antibody is used which binds the peptide in a manner restricting its rotational degrees of freedom such that the formation of this labile intermediate is favored. The intermediate itself is unstable, however, and as a result cannot be used to generate an antibody. A hapten is therefore used which approximates the steric and electronic conformation of the intermediate, but is of stable structure. This may be achieved, for example by replacement of the chiral carbon in the ring with a phosphorus atom in an oxidation state similar to that of the chiral carbon. For the above reaction, the result is a cyclic $\alpha$-amino phosphinate as shown in FIG. 4. This and other haptens of similar effect are prepared by conventional techniques.

Another hydrolysis method to which the invention may be applied is that involving the interaction of the carboxyl carbon of the adjacent peptide bond with the side chain of an adjacent amino acid. Side chains which may be used in this manner include asparagine, histidine, aspartate, glutamate, cysteine and serine. An example of such an interaction is one which produces a five-membered cyclic anhydride, the precursor of which is a five-membered heterocyclic ring containing an oxygen and four carbons, one of the carbons being a chiral tetrahedral carbon bonded to the ring oxygen, a ring carbon, and an oxygen and a nitrogen atom outside the ring. A structural representation of such a reaction, including the intermediate, is shown in FIG. 5, where the R group is an amino acid side chain.

Since the intermediate is an unstable transition state for the reaction, antibodies may be raised against an analogous hapten in which the chiral carbon is replaced by a phosphonate phosphorus atom, the heterocyclic ring of the hapten thus being a cyclic $\alpha$-amino phosphonate. As before, this and other haptens of similar effect are capable of preparation by conventional techniques.

Peptide bond cleavage has utility in a wide variety of contexts, including therapies for a variety of physiological conditions. One example is the hydrolysis of fibrin in the treatment of blood clots. Antibodies developed in accordance with the present invention will hydrolyze fibrin without the hemolytic activity associated with tissue specific plasminogen activator. Another example is the neutralization of the GP-120 viral coat target protein of the human immunodeficiency virus (HIV). Antibodies developed in accodance with the invention will bind to the protein and cleave it, thereby efficiently neutralizing the target. A still further example is the cleaving of fusion proteins to aid in protein sequencing or in generating semisynthetic proteins. This may be achieved by the use of a set of antibodies, such as for example a set of 10 to 20 or more antibodies, each having binding specificity for a designated dipeptide or tripeptide sequence.

3. Ligation of Peptide Fragments

The formation of peptide bonds between peptide fragments may also be rate enhanced by the present invention. Antibodies are used which have binding sites complementary to the two peptide fragments in an orientation in which an α-amino group on one fragment is in sufficient proximity to a carboxy ester on the other to promote the condensation which forms the peptide bond. Here, the antibody lowers the entropy barrier by restricting the translational degrees of freedom of the reactant pair. The antibody will accordingly be generated by a hapten which contains the same peptide fragments or analogues of them with similar steric and electronic features, joined in the appropriate orientation for the reaction to proceed. A phosphonate ester linkage or some other linkage may be used, joining the hapten components at sites corresponding to those where the α-amino and carboxy ester groups reside on the actual peptides, and preferably replacing both the α-amino and carboxy ester groups. The size of the linkage will be such that the spacing between the components approximates that of the reactant partners during the reaction.

In preferred situations, the hapten components will be joined in such a manner as to include the leaving group (i.e., the condensation by-product) as part of the structure. The resulting antibody binding site generated by such a hapten will thereby favor the reactant pair over the product, and product inhibition of the antibody will thus be avoided. A large leaving group such as a phenoxy anion (generating a phenol as the result of the condensation), is particularly effective since it significantly affects the steric character of the antibody binding site. The use of a phosphonate ester linkage between the hapten components further lessens product inhibition in view of steric difference between the tetrahedral phosphonate group and the peptide bond of the product.

This aspect of the invention is applicable to sequence specific peptide ligase in general. Examples include the joining of synthetic peptides to construct hormones and proteins. Further examples include the modifying of proteins or hormones at the carboxy or amino terminus with amino acids. Still further examples are the acylation of proteins (addition of R—CO—) and the amidation of proteins (addition of R—NH—).

Figure 6:
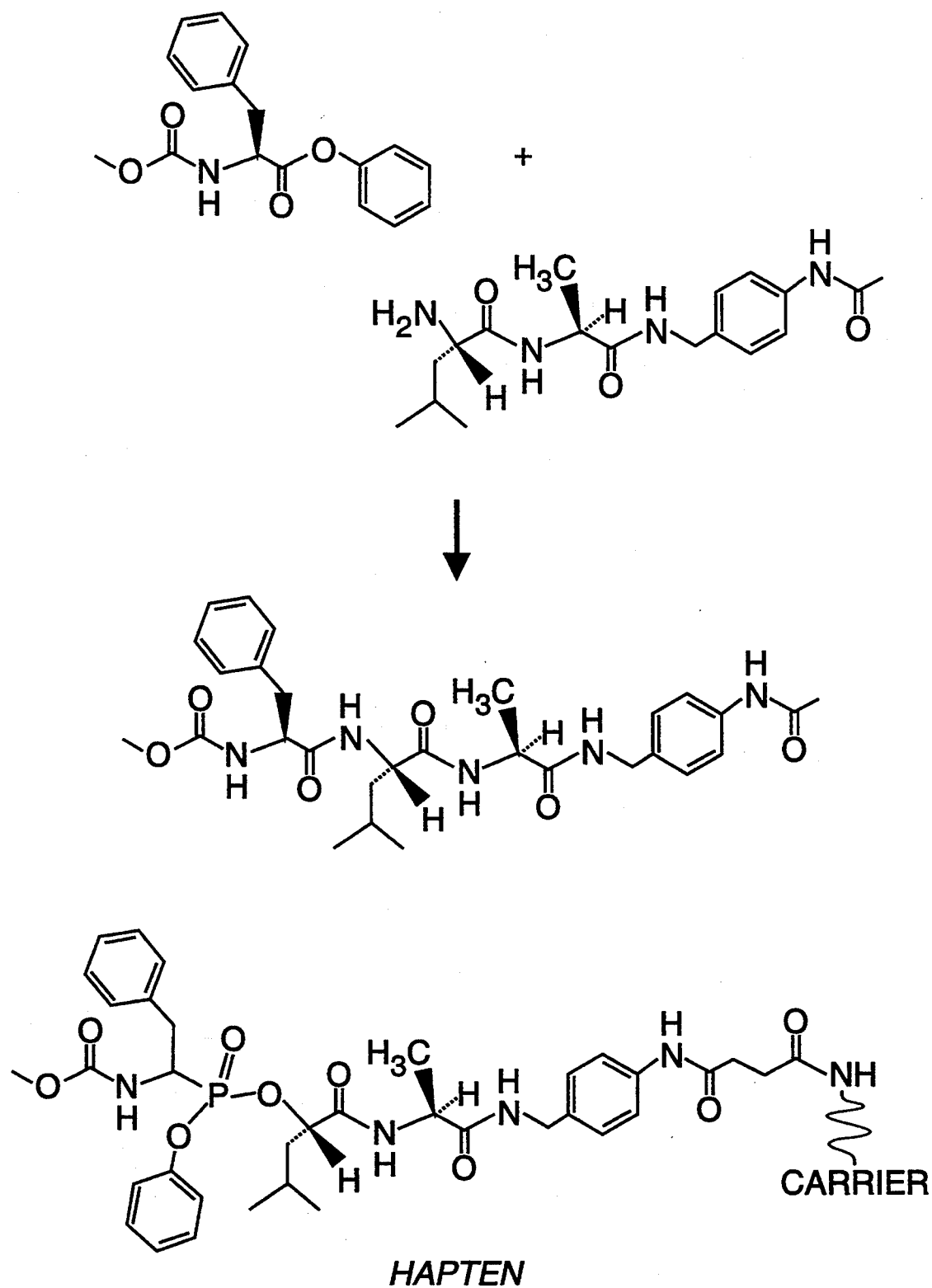
FIG. 6 illustrates a reaction involving the ligation of peptide fragments susceptible to acceleration by the invention, including a hapten suitable for generating the appropriate antibody.

An example of a ligation and the hapten used to generate the appropriate antibody is shown in FIG. 6. As before, this and other haptens of similar effect are capable of preparation by conventional techniques.

4. Cyclization Reactions

Cyclization reactions involving the formation of an ester or a peptide bond may also be rate enhanced by the present invention. The starting materials of interest are those in which the joining groups are separated by a chain of six or more atoms, preferably eight or more atoms, and most preferably ten or more atoms. Three types of cyclization are of interest in the context of the present invention—lactonization, cyclic peptide synthesis, and cyclic disulfide formation. The joining groups will accordingly be a carboxy ester-containing moiety and either a hydroxyl group or an amine, or, in the case of disulfide formation, two thiol moieties or a thiol and an activated thiol.

The antibodies used for rate enhancement of these reactions will favor the orientation of the starting material to place the joining groups in sufficient proximity and relative orientation to promote the reaction. Since the lactonization and cyclic peptide reactions proceed through a transition state with an unstable chiral tetrahedral carbon atom at the joining site, stable analogues in which the unstable carbon is replaced by a phosphorus atom in either a phosphonate or phosphinate form may be used as haptens. Other possible haptens are acetals and ketals. As in the other reactions discussed above, the tetrahedral character of the phosphorus atom is sufficiently different from the corresponding carbon atom in the reaction product (as opposed to the transition state) to lessen product inhibition. Also as discussed above, leaving groups in the condensation are preferably selected such that they offer further steric distinctions between the antibody binding site and the product, further lessening product inhibition. The cyclic disulfide formation may occur between two thiol groups through the use of mild oxidizing reagents as known in the art, or between a thiol and an activated thiol, i.e., one bearing a leaving group such as, for example, thiopyridone, again according to procedures known in the art. In the latter case, the hapten to induce cyclic disulfide formation will be the corresponding methylene analogue which includes an analogue of a leaving group such as thiopyridine. The antibody will then facilitate disulfide bond formation of a thiol and activated thiol moiety (thiopyridyl disulfide).

An example of a lactonization, showing the transition state as well as a suitable hapten, is shown in FIG. 7. The hapten shown may be prepared in accordance with conventional procedures. For instance, the appropriate protected alkyl aryl phosphite may be reacted with iodo chloro decane under Arbuzov conditions, followed by heating in the presence of iodide ion to give the protected cyclic phosphonate, which may then be deprotected under acidic conditions to form the desired product. The starting material for the cyclization reaction itself may be prepared by conventional techniques. One method involves the esterification of 9-decenoic acid with a halophenol, followed by treatment with $AcOBH_3$ and $H_2O_2$.

This aspect of the invention is useful in the synthesis of macrolide antibiotics, such as erythromycin, spiramycin, carbomycin, methymycin, narbomycin, lankamycin, chalcomycin, angolamycin, cephalosporins, penicillins, FK506, cyclosporin A, tyrocidin A, gramicidin S, actinomycins and somatostatin.

5. Glycosylations

A further class of reactions to which the present invention extends are glycosylations of such species as lipids, proteins or peptides, and sugars. In these reactions, the 1-carbon in the sugar being added bears an activated leaving group such as a phenolate group, a cyanomethyl group or a fluorine atom. The 1-carbon thus combines with a functional group on the other reactant by a condensation reaction. The functional group may be a hydroxyl group or an amino group, depending on the nature of the other reactant and the bond to be formed.

Antibodies are used which have binding sites complementary to both reactants in an orientation in which the 1-carbon in the sugar is in sufficient proximity to the functional group to promote the condensation which causes the glycosylation. Here, as in the previously described reactions, the antibody lowers the entropy barrier by favoring a specific orientation of the reactant pair over other possible orientations. The antibody will accordingly be generated by a hapten which contains the same species or analogues of them with similar steric and electronic features, joined in the appropriate orientation.

In the course of these reactions, the ring oxygen in the sugar being added passes through the oxonium form, and haptens may accordingly be prepared which have a positively charged group in the corresponding location. Antibodies raised by such haptens will stabilize the developing positive charge at the ring oxygen in the sugar reactant.

An example of the glycosylation of a sugar which is enhanced by the present invention is shown in FIG. 8, together with a hapten suitable for eliciting the appropriate antibody. Examples of possibilities for X and Y in this hapten are as follows:

| | |
|---|---|
| X = $NH_2^+$ | Y = $NH_2^+$ |
| X = $NH_2^+$ | Y = $CH_2$ |
| X = $CH_2$ | Y = $NH_2^+$ |
| X = $NH_2^+$ | Y = =N— |
| X = $NH_2^+$ | Y = O |
| X = O | Y = $NH_2^+$ |

Figure 9:
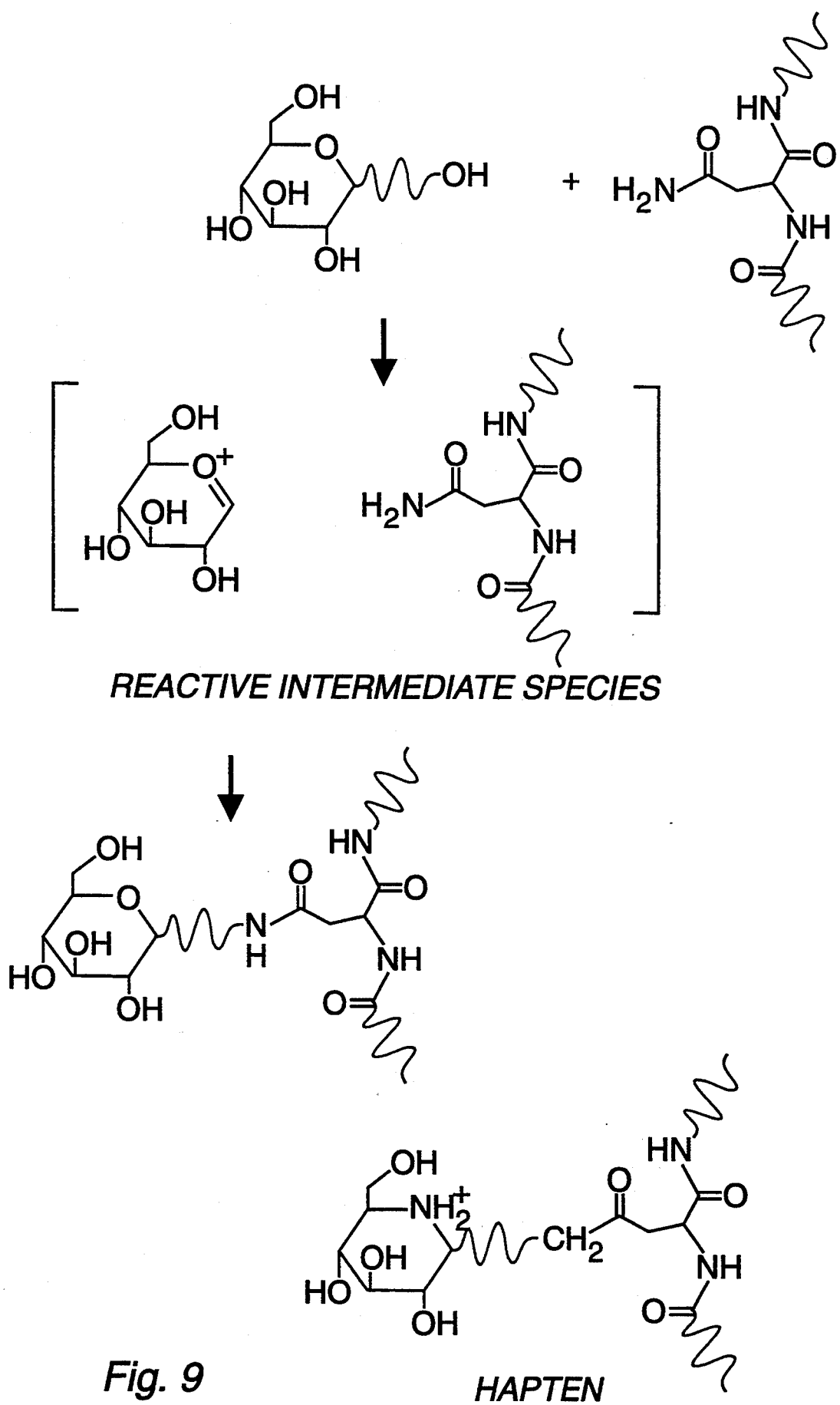
FIG. 9 illustrates a further type of glycosylation reaction susceptible to acceleration by the invention, including the transition state and a hapten suitable for generating the appropriate antibody.

The glycosylation of an asparagine is illustrated in FIG. 9. The activated leaving groups in these examples are represented by the symbol OR.

Preferred haptens are those which are conjugates of the reactants, i.e., analogues of the product, in which either the ring oxygen on the sugar being added or the functional group referred to above are replaced by an $NH_2^+$ group. Further preferred are those in which the ring oxygen has been replaced by an $NH_2^+$ group and the functional group is replaced by $NH_2^+$, $CH_2$ or =N—. These and other haptens of similar effect are capable of preparation by conventional techniques.

Glycosylations such as those described herein are useful in a variety of procedures. Examples are the post-translational modification of recombinant proteins or peptides with specific sugars to form peptide hormones, the synthesis of complex sugar moieties, and the synthesis of antibiotics such as sphingomycin.

6. Aldol Reactions

A further class of reactions to which the present invention is applicable are aldol reactions. These reactions include intramolecular cyclizations as well as bimolecular reactions. The critical transition state for one of the two moieties taking part in the reaction is that of an enolate anion in one of two resonance forms, the other resonance form tending toward the formation of an α-hydroxyalkyl alkenyl ether. The antibody used in accordance with the present invention will thus have a binding site complementary to the steric and electronic conformation of the critical resonance form leading to the aldol, further accomodating the carbonyl moiety with which the enolate anion combines, the carbonyl and enolate moieties being either on separate molecules or on the same molecule. The binding site will further hold the two together in an orientation which promotes the reaction. The antibody will accordingly be generated by a hapten prepared by conventional techniques which contains a molecule which approximates the steric and electronic conformation of the combined species in an orientation with respect to each other which leads to the aldol.

For example, with the aldol structure as follows:

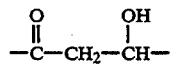

examples of haptens which may be used to raise antibodies are those which are analogues of the aldol in which the above group is replaced by either of the following:

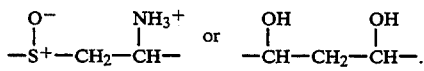

Antibodies in accordance with the present invention may be used to control the stereochemistry of aldols having a chiral carbon atom by the use of haptens having stereospecificity analogous to the desired aldol.

Figure 10:
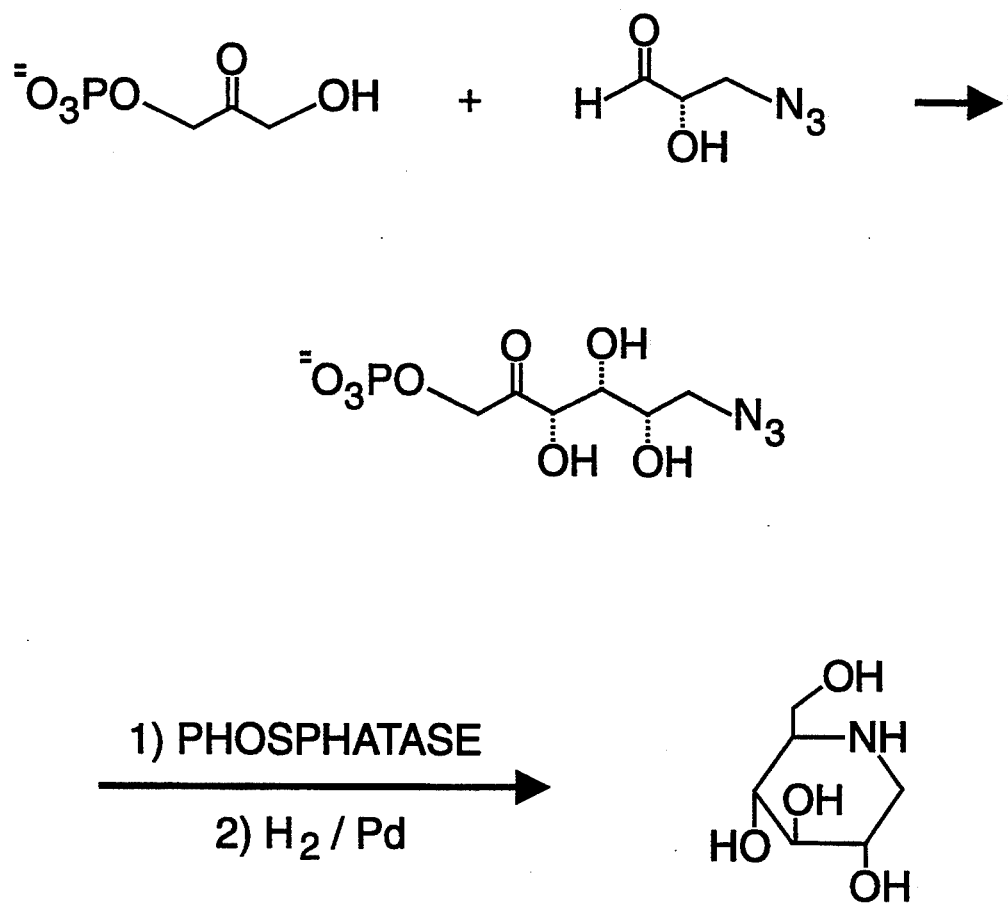
FIG. 10 illustrates an aldol reaction susceptible to acceleration and control by the invention.

Aldol reactions enhanced and controlled in this manner as useful in a variety of syntheses. Examples are syntheses of deoxynojirimycin, sialic acid, mannose and galactose. An illustration of deoxynojirimycin synthesis through an aldol reaction using the present invention is shown in FIG. 10.

7. Nucleoside Synthesis

A still further class of reactions susceptible to rate enhancement by the present invention are nucleoside synthesis reactions. These reactions involve the coupling of purine, pyrimidine or an analogue of either of these bases (such as for example a deaza analogue) to either D-ribose or 2-deoxy-D-ribose, or derivatives thereof, by a condensation reaction promoted by a leaving group attached to the 1-carbon of the D-ribose or 2-deoxy-D-ribose. Examples of such leaving groups are a bromine atom, a fluorine atom and a pyrophosphate group:

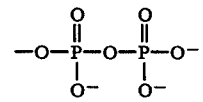

Examples of appropriate haptens for the generation of rate-enhancing antibodies for these reactions are analogues of the nucleoside products in which the leaving group or a group similar to it in its atetic and electronic character is still present, thereby representing the transition state. The presence of this group in the hapten further lessens product inhibition, as in the other reactions discussed above.

Figure 11:
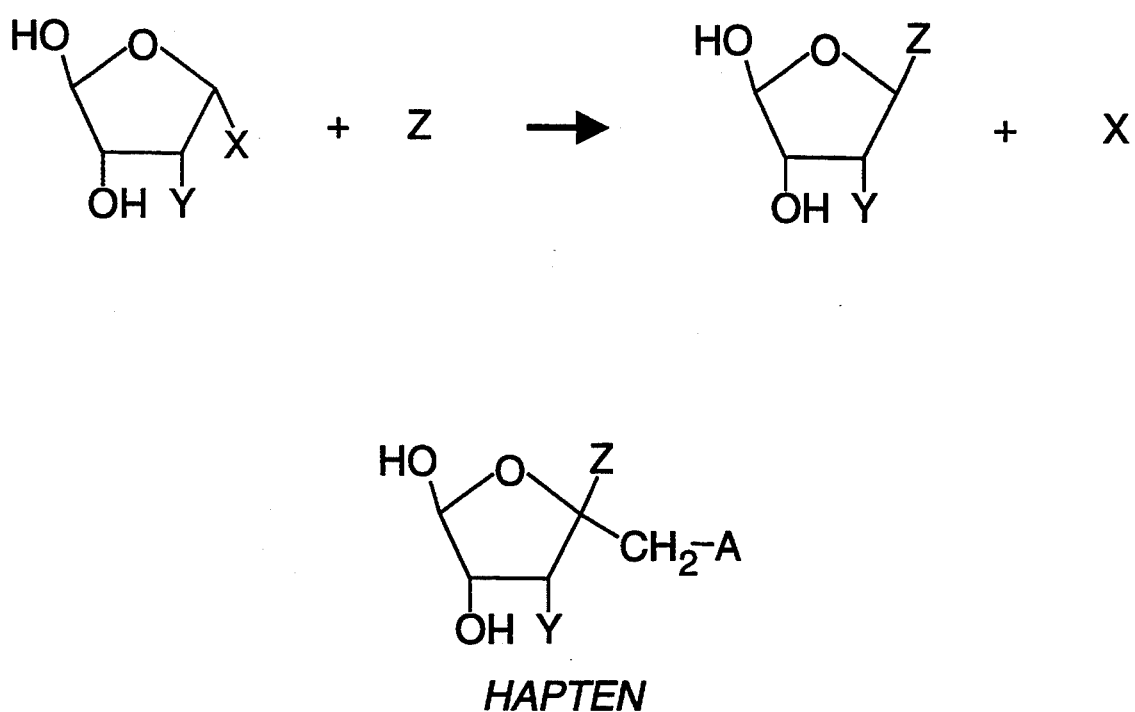
FIG. 11 illustrates a nucleoside synthesis reaction susceptible to acceleration by the invention, including a hapten suitable for generating the appropriate antibody.

An illustration of a nucleoside synthesis in accordance with the invention is shown in FIG. 11, together with a hapten suitable for generating the appropriate antibody. In this illustration, the symbol Y represents H or OH; X represents the leaving group, Z represents the base; and —$CH_2$—A represents the leaving group analogue.

Examples of syntheses where this aspect of the invention finds application are syntheses of nucleoside antibiotics such as 2'-fluoroguanine, azidothymidine, acycloguanosine, formycin, tubercidin, and cordycepin.

8. Transesterification Reactions

A still further class of chemical reactions susceptible to rate enhancement by the present invention are those involving the transesterification of alcohols with acyl groups. Here again, the antibody is one which has a binding site of appropriate steric and electronic character to form an environment complementary to the combined reactant pair in the orientation necessary for the reaction to proceed. A conjugate analogue of the starting materials may be used as the hapten, the components of the conjugate joined by a phosphonate ester linkage with the phosphorus atom in a position corresponding to the acyl carbon. The inclusion of a leaving group or an analogue thereof in the phosphonate moiety will, as in the reactions discussed above, lessen the tendency toward product inhibition.

Figure 12:
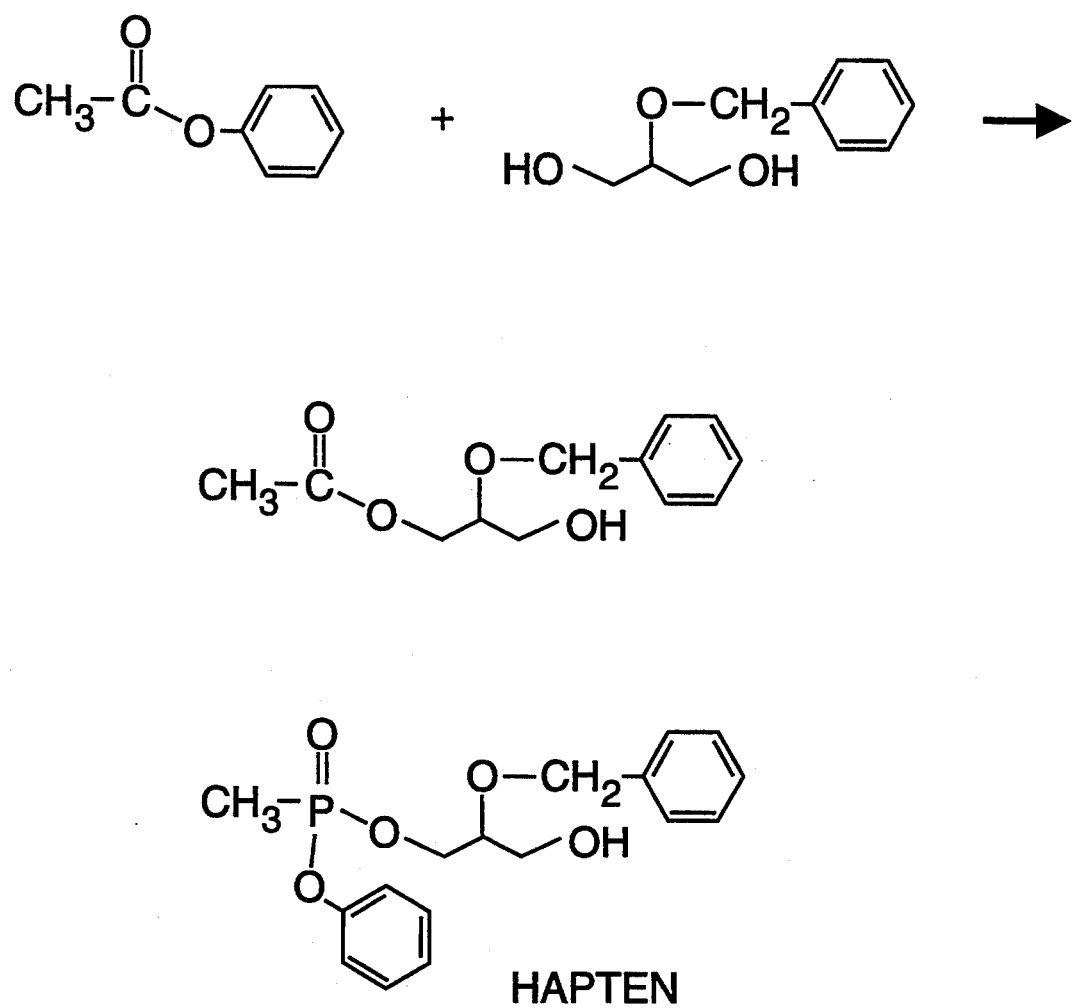
FIG. 12 illustrates a transesterification reaction susceptible to acceleration by the invention, including a hapten suitable for generating the appropriate antibody.

An example of a transesterification of an alcohol with an acyl group to which the invention may be applied is shown in FIG. 12, together with an appropriate hapten.

Figure 13:
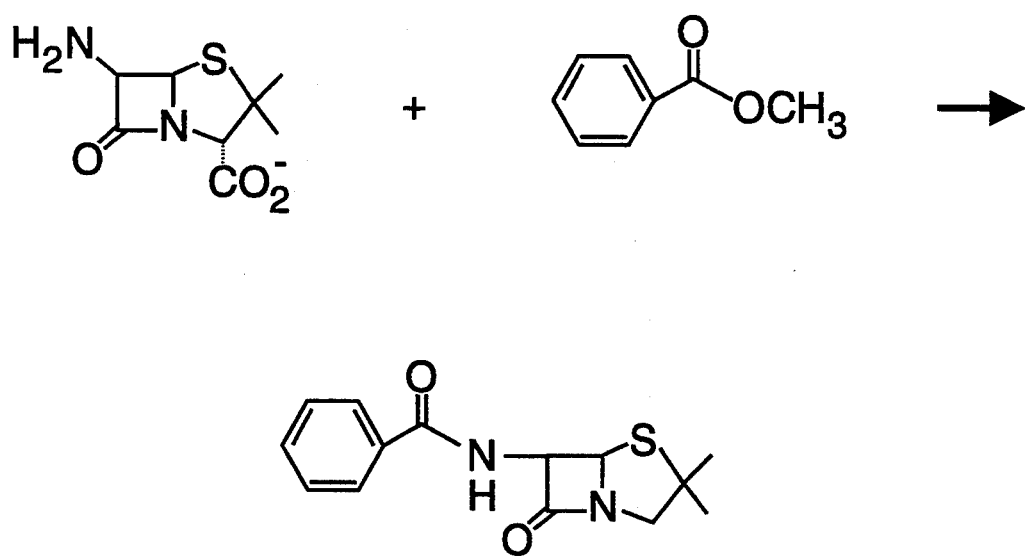
FIG. 13 illustrates an amide bond formation susceptible to acceleration by the present invention.

A variation of this reaction is the combination of an amine with a a compound bearing an acyl group. The product in this case will be an amide bond joining the reactants. An example of this type of reaction is the introduction of an acyl side chain into a $\beta$-lactam antibiotic, illustrated in FIG. 13. Here again, one may use as the hapten a phosphonate diester analogue of the product, preferably with the inclusion of a leaving group in the same manner as the alcohol/acyl group reaction.

In each of these classes of reactions, antibodies for use in accordance with the present invention may be obtained by injecting the hapten-carrier conjugate into a wide variety of vertebrates in accordance with conventional techniques. Suitable vertebrates include mice, rats, sheep, goats and rabbits. According to these techniques, the animals are bled periodically, successive bleeds having improved titer and specificity. The conjugates may be injected intramuscularly, intraperitoneally, subcutaneously, or the like. Usually, a vehicle is employed, such as a complete or incomplete Freund's adjuvant.

The carrier used in the hapten-carrier conjugate may be any conventional immunogenic carrier. Examples of immunogenic carriers are human $\gamma$-globulin, human serum albumin, hare serum albumin, bovine $\gamma$-globulin, bovine serum albumin, egg ovalbumin, keyhole limpet hemocyanin, as well as polypeptides such as polymers of lysine, polymers of glutamic acid and the like. The hapten will be coupled to the immunogenic carrier through a spacer arm in the conventional manner, the length of the spacer arm being sufficient to avoid steric interference between the hapten and the carrier. A typical spacer arm may have a length of about 6 Å to about 8 Å.

To obtain monoclonal antibodies, spleen cells from the immunized vertebrate are immortalized. The manner of immortalization is not critical. Presently, the most common method is fusion with a myeloma fusion partner. Other techniques include EBV transformation, transformation with bare DNA such as oncogenes, retroviruses or the like, or any other method which provides for the stable maintenance of the cell line and production of monoclonal antibodies. The antibodies may be of any immunoglobulin class, including $IgG_1$, $IgG_{2A}$, $IgG_{2B}$, IgA, IgD, IgE and IgM. Antibodies of the classes IgG and IgM are preferred.

With the assistance of the antibodies, the reactions may be conducted in the absence of other catalysts, and at temperatures substantially lower than those at which the uncatalyzed reactions are conventionally run. In many cases, the reactions may be conducted substantially at room temperature.

The following example is offered by way of illustration, not by way of limitation.

EXAMPLE

This example illustrates the Claisen rearrangement shown in FIG. 1, catalyzed by antibody in accordance with the present invention.

1. Preparation of Hapten a.
($\pm$)-(3-endo-8-exo)-8-[(4-Nitrophenylpropyl)carbamoyloxy]-2-oxabicyclo-[3.3.1]non-6-ene-3,5-dicarboxylic Acid Dimethyl Ester A solution of 79 mg (0.38 mmol) of p-nitrophenylbutyric acid, 156 mg (0.57 mmol) of diphenylphosphoryl azide, and 0.1 mL (0.57 mmol) of triethylamine, in 0.5 mL of benzene, was refluxed for 2 h, then allowed to cool to 21° C. The dimethylester-alcohol (97 mg, 0.38 mmol) in 0.5 mL benzene was added to the resulting isocyanate solution via canula, and the resulting mixture was refluxed for 12 h. After dilution with 10 mL of $CH_2Cl_2$, the reaction mixture was washed with unsaturated aqueous $NaHCO_3$, dried over $Na_2SP_4$, and evaporated to afford 398 mg of a yellow oil.

Purification on $SiO_2$ (5:1 diethyl ether:hexanes) yielded 145 mg (83%) of the carbamate as a white foam. An analytical sample was obtained by preparative thin-layer chromatography (10% $CH_3OH/CH_2Cl_2$, triple elution). Product structure was confirmed by IR (film 3380, 2850, 1730, 1520, 1350 cm$^{-1}$; $^1$H NMR (CDCl$_3$) $\delta$ 8.14 (d, 2, J=8.6), 7.34 (d, 2, J=8.6), 6.10 (d, 1, J=10.0), 5.90 (dd, 1, J=10.0, 3.8), 5.32 (bs, 1), 4.76 (bt, 1, J=5.4), 4.44 (d, 1, J=6.8), 4.25 (bs, 1), 3.76 (s, 3), 3.71 (s, 3), 3.23 (apparent q, 2, J=6.7), 2.76 (t, 2, J=7.6), 2.6 (m, 1), 2.22 (dd, 1, J=7.5, 6.2), 2.02 (bs, 2), 1.87 (apparent quint, 2, J=7.3); elemental analysis calculated for $C_{22}H_{26}O_9N_2$: C, 57.14; H, 5.66; N, 6.06; found: C, 56.94; H, 5.74; N, 5.99.

b.
($\pm$)-(3-endo-8-exo)-8-[(4-Aminophenylpropyl)carbamoyloxy]-2-oxabicyclo-[3.3.1]non-6-ene-3,5-dicarboxylic Acid Dimethyl Ester To 63 mg (0.14 mmol) of the nitrocarbamate in 1 mL of 2:1 methanol:ethanol was added 5 mg of $PtO_2$, and the resulting slurry was stirred under a hydrogen atmosphere for twenty minutes. The product was isolated by filtration of the reaction mixture through glass wool and evaporation to give 56 mg of the crude amine.

Preparative thin-layer chromatography (5% $CH_3OH/CH_2Cl_2$, double elution) afforded 44 mg (75% yield) of the pure carbamate as a colorless foam: IR (CHCl$_3$) 3450, 3400, 3010, 2960, 1730, 1620, 1510, 1250 cm$^{-1}$; $^1$H NMR (CDCl$_3$) $\delta$ 6.95 (d, 2, J=8.2), 6.64 (d, 2, J=8.2), 6.09 (d, 1, J=10.0), 5.92 (dd, 1, J=0.9, 4.5), 5.31 (bs, 1), 4.60 (bs, 1), 4.44 (d, 1, J=7.2), 4.26 (bs, 1), 3.76 (s, 3), 3.73 (s, 3), 3.58 (bs, 2), 3.20 (apparent q, 2, J=6.6), 2.61 (d, 1, J=15.8), 2.53 (t, 2, J=7.4), 2.22 (dd, 1, J=7.5, 13.6), 2.04 (bs, 2), 1.77 (apparent quintet, 2, J=7.3); FAB+ MS m/z 432 (MH+, 100), 239 (20), 211 (45); HRMS (FAB+), calculated for $C_{22}H_{28}O_7N_2$: m/z 432.1897; found: m/z 432.1907.

($\pm$)-(3-endo-8-exo)-8-[(4-Aminophenylpropyl)carbamoyloxy]-2-oxabicyclo-[3.3.1]non-6-ene-3,5-dicarboxylic Acid Bis(triethylammonium) Salt A solution of 38 mg (0.08 mmol) of the dimethyl ester in 4 mL of 50% aqueous methanol and 1.05 mL of 0.5N NaOH was kept at 21° C. for 3 hours. The solution was diluted with 15 mL of 1N triethylammonium bicarbamate (pH 8) and lyophilized. The residual solid was dissolved in 4 mL of water and applied to a DEAE Sephadex column (ammonium form, 10 mL), which was eluted with a gradient from 0.5 to 1.0M triethylammonium bicarbonate.

Lyophilization of the fractions containing product afforded 54 mg (100%) of the bis(triethylammonium) salt as a hygroscopic white solid: $^1$H NMR (D$_2$O) δ 6.83 (d, 2, J=8.0), 6.53 (d, 2, J=8.0), 5.92 (d, 1, J=9.9), 5.47 (dd, 1, J=4.3, 10.1), 4.93 (bs, 1), 3.96 (dd, 1, J=4.3, 7.1), 3.92 (bs, 1), 2.85 (t, 2, J=6.3), 2.70 (q, 6, J=7.3), 2.67 (t, 6, J=7.3), 2.29 (t, 2, J=7.3), 2.0 (dd, 1, J=7.1, 13.1), 1.70 (m, 2), 1.50 (t, 2, J=6.8), 0.93 (t, 18, J=7.3); $^{13}$C NMR (D$_2$O) δ 184.0, 180.7, 158.6, 144.8, 138.8, 133.9, 130.2, 124.5, 117.6, 72.0, 71.1, 68.7, 47.2, 42.4, 41.0, 34.2, 32.4, 31.7, 29.6, 9.8; HRMS (FAB+) calculated for C$_{32}$H$_{54}$O$_7$N$_4$: m/z 404.1584; found: m/z 404.1589.

2. Preparation of Substrates and Products

Chorismic acid (Sigma Chemical Co., St. Louis, Mo.) was purified by preparative reverse phase HPLC and recrystallized twice from ether-methylene chloride-hexane (1:1:2). Prephenic acid was prepared by heating an aqueous solution of chorismate, pH 5.0, to 65° C. for two hours followed by purification using preparative reverse phase HPLC.

3. Preparation of Carrier Protein Conjugates

To 10 mg of hapten (16.6 μmoles) in 146 μL of aqueous 1M HCl at 0° C. was added one equivalent (1.13 mg) of NaNO$_2$ in 45 μL ice-cold water. After stirring for 5 minutes, the resulting mixture was added in one portion to a cooled (0° C.) solution of 25 mg carrier protein, which was either bovine serum albumin (BSA) or keyhole limpet hemocyanin (KLH) in 1.42 mL of aqueous 0.04M NaOH. The resulting dark red solution was stirred at 0° C. for 2 hours and then allowed to stand at 0° C. for 4 hours. The pH was then adjusted to 7.7 by the addition of dilute HCl and the conjugate exhaustively dialyzed at 4° C. against aqueous 10 mM phosphate, 150 mM NaCl, pH 7.4, buffer. Protein concentrations were determined by the method of Lowry, O. T., et al., *J. Biol. Chem* 193: 265 (1951), and epitope densities (BSA=5, KLH monomer=12) by the absorbance of the azo linkage (370 nm, ε ca, 22,000).

4. Purification of Antibodies

Monoclonal antibodies were purified at 4° C. from ascites fluid using standard procedures as follows.

Ascites fluid (10 mL) was diluted with 20 mL binding buffer (1.5M glycine, 3M NaCl, pH 8.9), clarified by centrifugation at 10,000× g for 15 minutes, then filtered through a glass wool plug. The filtrate was applied (flow rate=30 mL/h) to a Protein-A coupled Sepharose 4-B column previously equilibrated with binding buffer and the column washed until the protein absorbance (280 nm) was below 0.05 AU. Antibody was eluted with 0.1M aqueous citrate pH 3.0, buffer in 2.5 mL fractions into test tubes containing 0.8 mL of 1.0M aqueous Tris.HCl, pH 9.0, buffer. Fractions were assayed by A$_{280}$ and the eluted protein was pooled and exhaustively dialyzed against the assay buffer. The antibody was determined to be homogeneous by sodium dodecylsulfate-polyacrylamide gel electrophoresis with Coomasie blue staining.

5. Use of Antibodies to Catalyze the Rearrangement

The rearrangement of the purified chorismic acid to prephenic acid was assayed spectrophotometrically (270 nm) at pH 7.0 (5 mM NaCl, 50 mM Na$_2$PO$_4$ buffer) in both the absence and presence of antibody. The reactions were followed at 10° C. to minimize subsequent decomposition of prephenate. One of eight antibodies (IgG) assayed was found to catalyze the Claisen rearrangement, with initial rates consistent with the Michaelis-Menten rate expression:

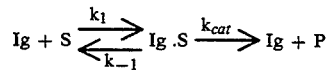

where S denotes the substrate (chorismic acid) and P denotes the product (prephenic acid). The values of Kcat and the Michaelis constant K$_m$ were 2.7 min$^{-1}$ and 260 μM, respectively, at 10° C. HPLC analysis confirmed that the sole product (>99%) of the antibody-catalyzed reaction was prephenic acid. The uncatalyzed reaction afforded a mixture of prephenate and p-hydrobenzoate in a molar ratio of 19 to 1.

The foregoing is offered primarily for purposes of illustration. It will be readily apparent to those skilled in the art that numerous modifications, substitutions, and alternative methods may be employed beyond those disclosed herein, without departing from the spirit and scope of the invention.

What is claimed is:

1. A monoclonal antibody having binding specificity for a cyclic transition state species in a pericyclic chemical reaction, which pericyclic chemical reaction involves both the redistribution of electrons in a pair of double bonds to form a new double bond and the conversion of at least one of said pair of double bonds to a single bond, in which said cyclic transition state species contains a transitional six-membered ring present only in said transition state, said six-membered ring having a chair-like configuration.

2. An antibody having binding specificity for a cyclic transition state species in a pericyclic chemical reaction, which pericyclic chemical reaction involves both the redistribution of electrons in a pair of double bonds to form a new double bond and the conversion of at least one of said pair of double bonds to a single bond, in which said antibody is a monoclonal antibody.

3. A monoclonal antibody having binding specificity for a cyclic transition state species in a pericyclic chemical reaction, which pericyclic chemical reaction involves both the redistribution of electrons in a pair of double bonds to form a new double bond and the conversion of at least one of said pair of double bonds to a single bond, in which said pericyclic chemical reaction is an intramolecular rearrangement.

4. An antibody in accordance with claim 3 in which said intramolecular rearrangement is one whose uncatalyzed free entropy of activation is less than about −5 eu.

5. An antibody in accordance with claim 3 in which said intramolecular rearrangement is one whose uncatalyzed free entropy of activation is less than about −10 eu.

6. An antibody in accordance with claim 3 in which said intramolecular rearrangement is a Claisen rearrangement.

7. An antibody in accordance with claim 3 in which said intramolecular rearrangement is a Claisen rearrangement of an alkenyl ether of an enol to a γ,δ-unsaturated ketone.

8. An antibody in accordance with claim 3 in which said intramolecular rearrangement is a Claisen rearrangement of a cycloalkenyl ether of an enol to a γ,δ-unsaturated ketone.

9. An antibody in accordance with claim 3 in which said intramolecular rearrangement is a Claisen rearrangement of a 2,4-cyclohexadienyl ether of an enol to a β-2,5-cyclohexadienyl ketone.

10. An antibody in accordance with claim 9 in which said antibody is one which has been raised against a hapten which is a stable analog of said cyclic transition state species containing a cyclic group comprised of single bonds, double bonds or a combination thereof.

11. An antibody in accordance with claim 9 in which said cyclic transition state species contains a transitional six-membered ring present only in said transition state, said six-membered ring having a chair-like configuration, and said antibody is one which has been raised against a hapten which has substantially the same antibody-binding specificity as said cyclic transition state species except that the portion thereof corresponding to said six-membered ring is comprised entirely of single bonds.

* * * * *